United States Patent
Yamada et al.

(10) Patent No.: US 10,240,917 B2
(45) Date of Patent: Mar. 26, 2019

(54) MEASURING APPARATUS AND MEASURING METHOD

(71) Applicant: KYOCERA Corporation, Kyoto-shi, Kyoto (JP)

(72) Inventors: Tomoya Yamada, Moriyama (JP); Taku Matsudera, Otsu (JP)

(73) Assignee: Kyocera Corporation, Kyoto (JP)

( * ) Notice: Subject to any disclaimer, the term of this patent is extended or adjusted under 35 U.S.C. 154(b) by 0 days.

(21) Appl. No.: 15/545,478

(22) PCT Filed: Jan. 22, 2016

(86) PCT No.: PCT/JP2016/051882
§ 371 (c)(1),
(2) Date: Jul. 21, 2017

(87) PCT Pub. No.: WO2016/117691
PCT Pub. Date: Jul. 28, 2016

(65) Prior Publication Data
US 2018/0010908 A1    Jan. 11, 2018

(30) Foreign Application Priority Data

Jan. 23, 2015   (JP) .................................. 2015-011238

(51) Int. Cl.
*G01B 11/30*   (2006.01)
*G01N 21/47*   (2006.01)
(Continued)

(52) U.S. Cl.
CPC .............. *G01B 11/30* (2013.01); *B07C 5/342* (2013.01); *G01N 21/47* (2013.01); *G01N 21/9508* (2013.01)

(58) Field of Classification Search
CPC ................................. G01B 11/30; G01N 21/47
(Continued)

(56) References Cited

U.S. PATENT DOCUMENTS 4,834,539 A * 5/1989 Le Bris .................. G01N 21/03
356/244
2005/0112115 A1    5/2005 Khan
(Continued)

FOREIGN PATENT DOCUMENTS

JP    H10-269682 A    10/1998
JP    2002-350283 A   12/2002
(Continued)

OTHER PUBLICATIONS

International Search Report dated Apr. 26, 2016, issued by Japan Patent Office for International Application No. PCT/JP2016/051882.

*Primary Examiner* — Sunghee Y Gray
(74) *Attorney, Agent, or Firm* — Procopio Cory Hargreaves and Savitch LLP (57) ABSTRACT

A measuring apparatus according to the present disclosure includes a support plate and an optical sensor. The support plate has an upper surface on a central portion of which an object is to be mounted, and is rotatable about an axis of rotation extending vertically from the central portion. The optical sensor is disposed above the support plate, and has a light-emitting element configured to irradiate the object with light and a light-receiving element configured to receive reflection light reflected from the object.

8 Claims, 5 Drawing Sheets

(51) Int. Cl.
*B07C 5/342* (2006.01)
*G01N 21/95* (2006.01)

(58) Field of Classification Search
USPC .......................................................... 356/600
See application file for complete search history.

(56) References Cited

U.S. PATENT DOCUMENTS

| | | | |
|---|---|---|---|
| 2007/0164240 A1 | 7/2007 | Shinno et al. | |
| 2010/0328669 A1 | 12/2010 | Myrick et al. | |
| 2013/0033595 A1* | 2/2013 | Adelson ............... | A61B 5/0077 348/92 |
| 2013/0258326 A1 | 10/2013 | Horie et al. | |
| 2014/0110606 A1* | 4/2014 | Furukawa .............. | G01B 11/30 250/492.2 |

FOREIGN PATENT DOCUMENTS

| | | | | |
|---|---|---|---|---|
| JP | 2002350283 | * | 12/2002 | |
| JP | 2007-187570 A | | 7/2007 | |
| JP | 2011-197012 A | | 10/2011 | |
| JP | 2011197012 | * | 10/2011 | |
| JP | WO2013065731 | * | 10/2013 | ............. G01B 11/30 |
| JP | 2013-253030 A | | 12/2013 | |
| JP | 2014-199692 A | | 10/2014 | |

\* cited by examiner

MEASURING APPARATUS AND MEASURING METHOD

TECHNICAL FIELD

The present invention relates to a measuring apparatus and a measuring method.

BACKGROUND ART

For example, as described in Japanese Unexamined Patent Publication JP-A 2007-187570, there is a heretofore known apparatus that detects a surface roughness of a measurement surface of an object to be measured by irradiating the object with light from a light-emitting element and receiving reflected light from the object with a light-receiving element.

SUMMARY OF INVENTION

A measuring apparatus according to the present disclosure comprises a support plate and an optical sensor. The support plate comprises an upper surface on a central portion of which an object is to be mounted, and is rotatable about an axis of rotation extending vertically from the central portion. The optical sensor is disposed above the support plate, and comprises a light-emitting element configured to irradiate the object with light and a light-receiving element configured to receive reflection light reflected from the object.

A measuring method according to the present disclosure comprises: placing an object in the measuring apparatus described above; securing the optical sensor of the measuring apparatus in a position where one point of the object is irradiated with light; and receiving reflected light from the object by the light-receiving element of the optical sensor while rotating the support plate in a state where the optical sensor is secured in the position.

DESCRIPTION OF EMBODIMENTS

<Measuring Apparatus>

One embodiment of a measuring apparatus according to the present disclosure will be described with reference to FIGS. 1 to 5. It should be understood that the application of the invention is not limited to the present embodiment, and that various changes, modifications, and improvements are possible without departing from the scope of the invention.

Figure 1:
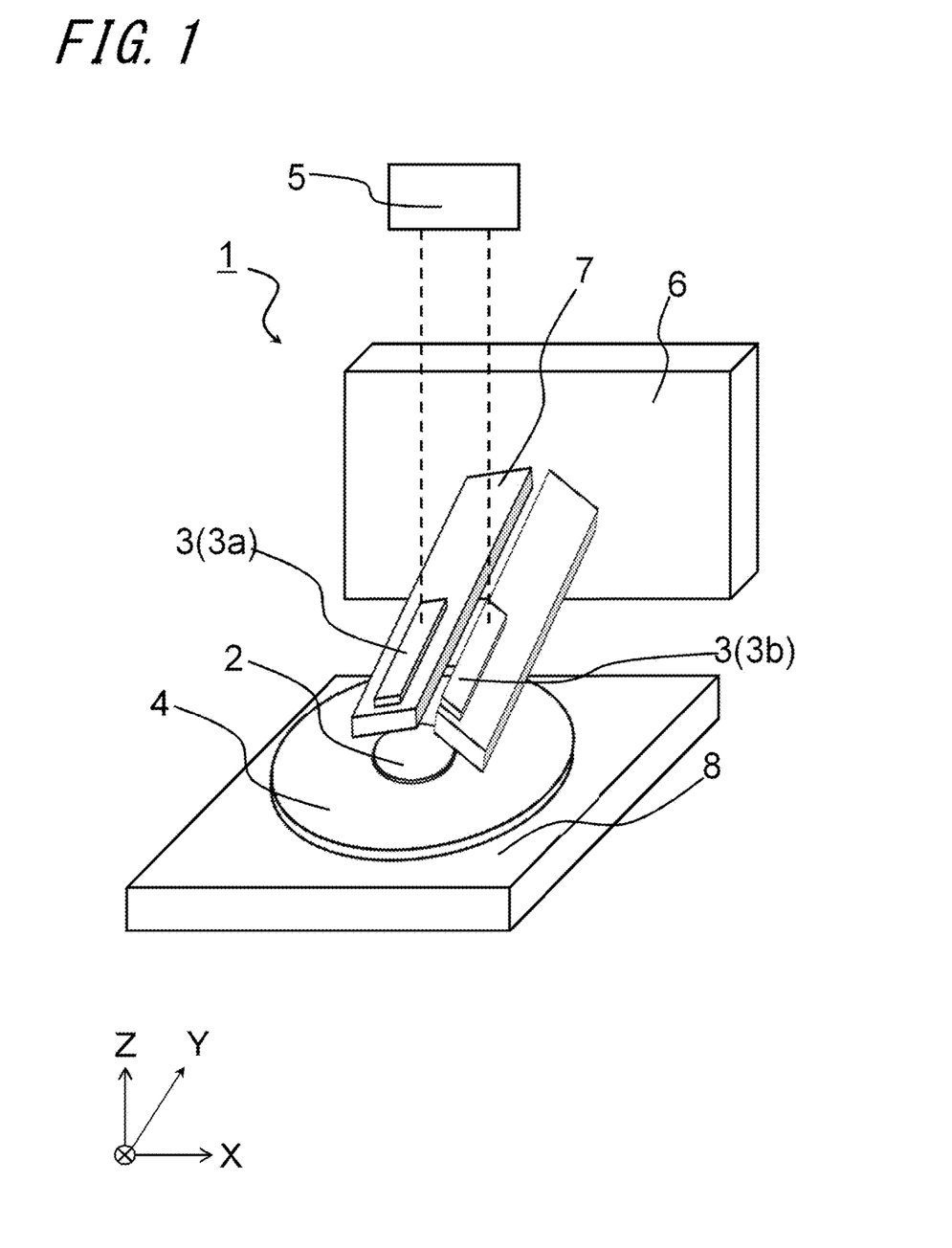
FIG. 1 is a perspective view schematically showing a measuring apparatus according to the present disclosure.
Figure 2:
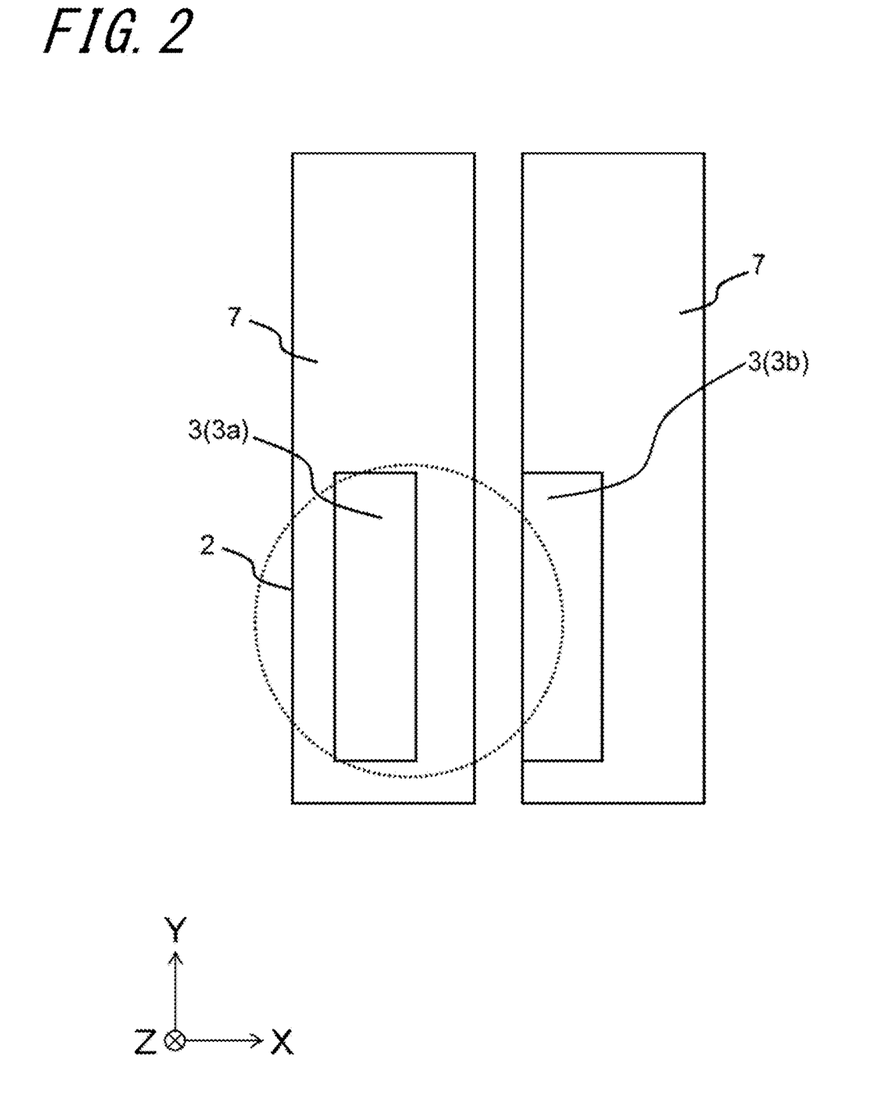
FIG. 2 is a top view schematically showing the measuring apparatus according to the present disclosure.
Figure 3:
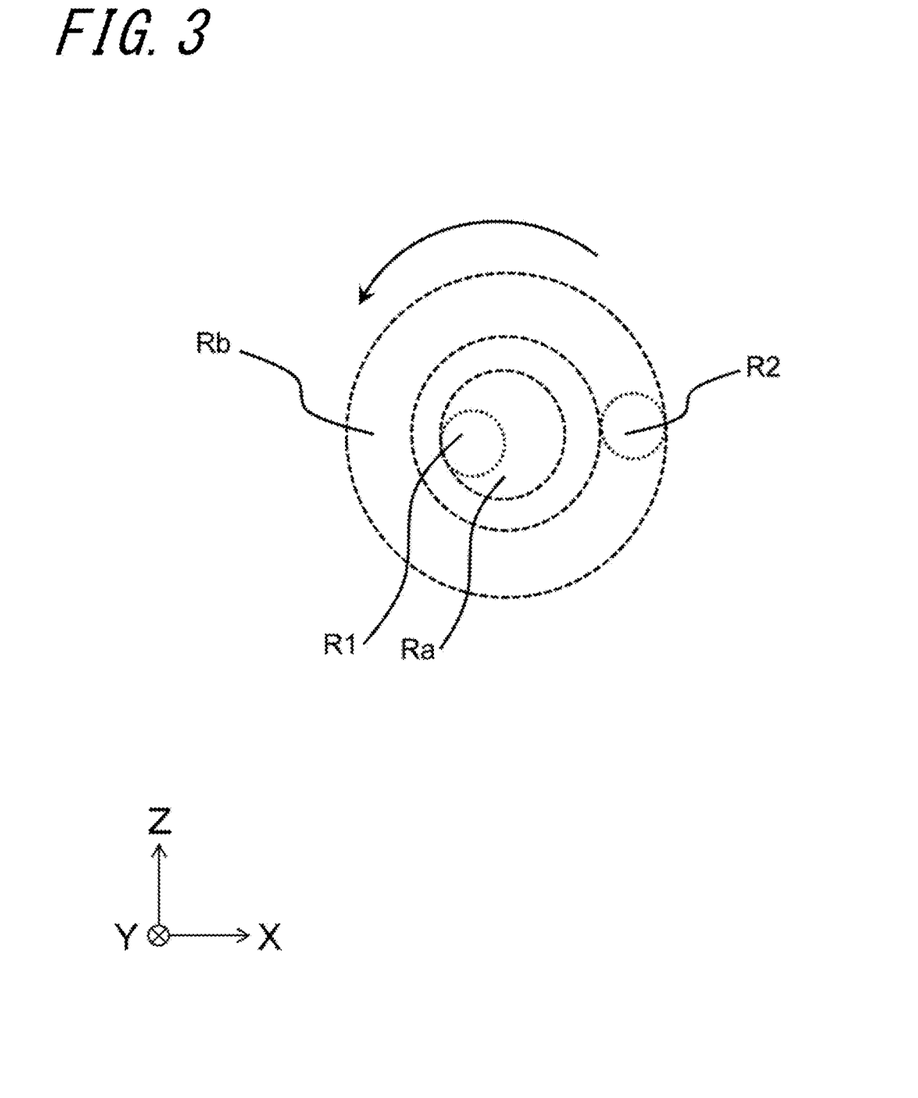
FIG. 3 is a top view schematically showing the measuring apparatus according to the present disclosure.
Figure 4:
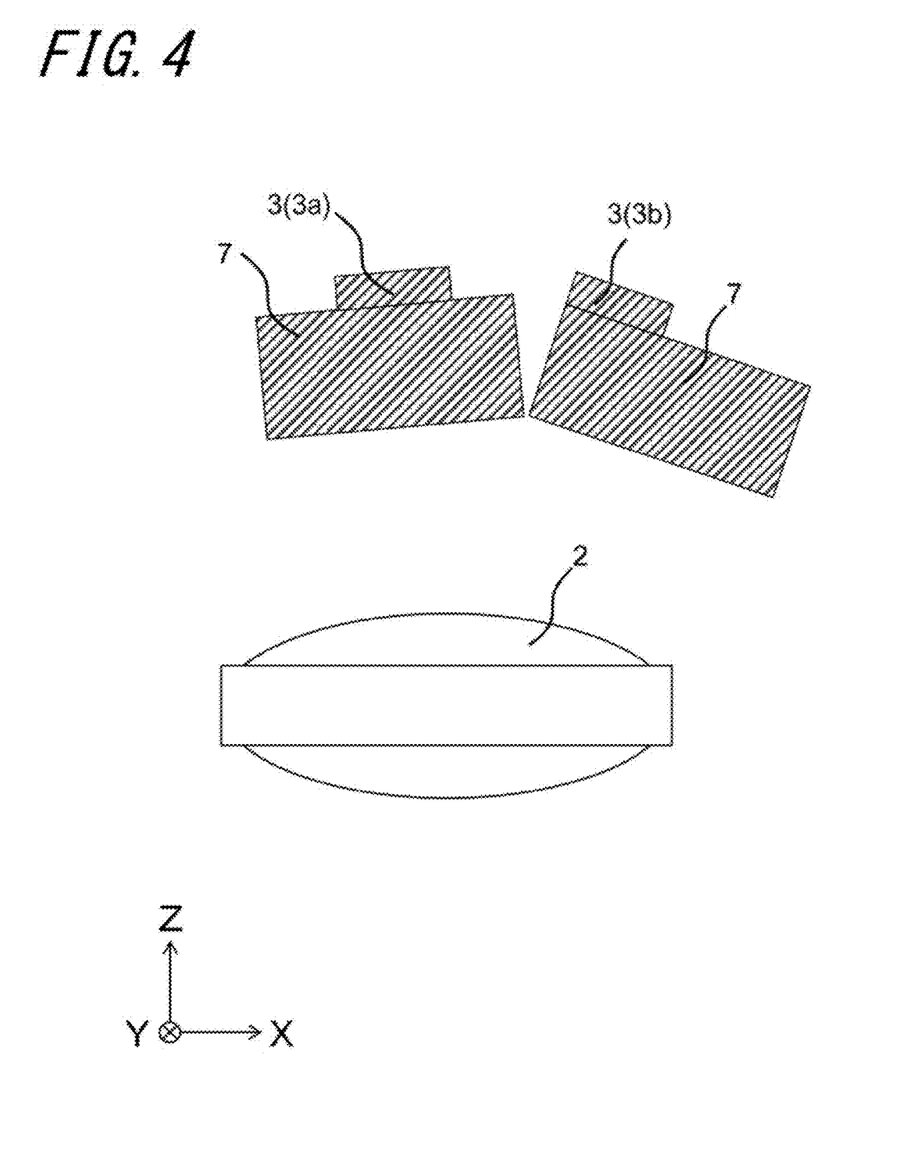
FIG. 4 is a sectional view schematically showing the measuring apparatus according to the present disclosure.
Figure 5A:
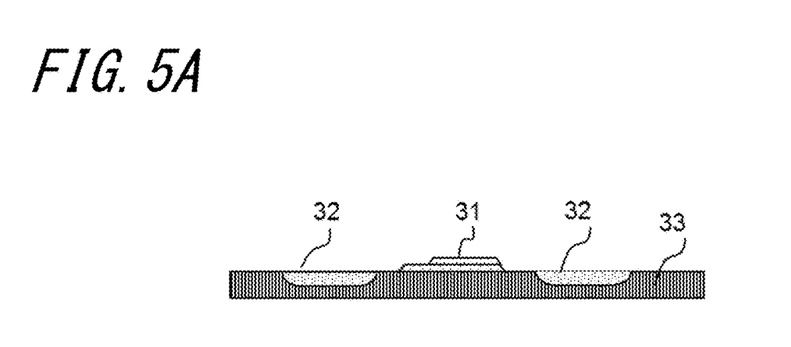
FIGS. 5A and 5B are sectional views schematically showing an optical sensor provided in the measuring apparatus according to the present disclosure.
Figure 5B:
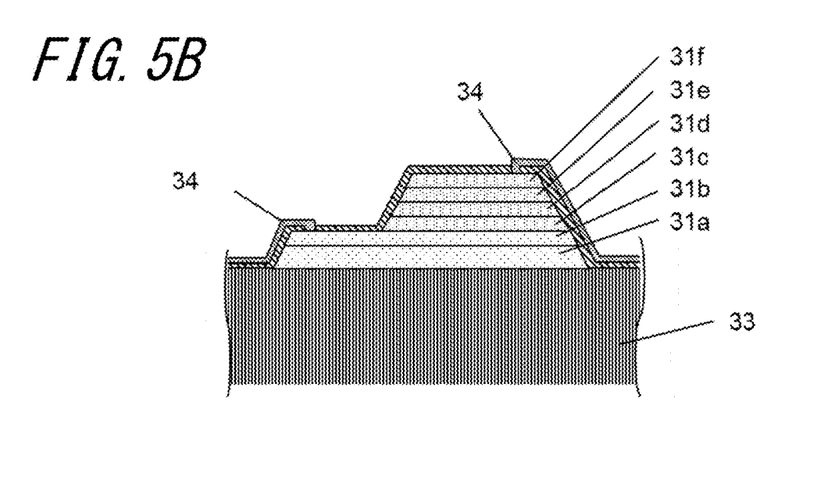

FIG. 1 is a general view of a measuring apparatus. FIG. 2 is a view illustrating a positional relationship between a support plate and an optical sensor in the measuring apparatus. FIG. 3 is an explanatory view of a measurement region of an object to be measured by the measuring apparatus. An arrow depicted in FIG. 3 indicates the direction of rotation of the object. FIG. 4 is a view illustrating a positional relationship between the support plate and the optical sensor in the measuring apparatus. FIG. 5A is a general schematic view of the optical sensor, and FIG. 5B is a schematic view of a light-emitting element.

For example, the measuring apparatus 1 is capable of measurement of the surface roughness of an object 2, or the surface conditions, such as the degrees of coarseness and fineness, of the surface of the object 2. A measurement surface of the object 2 may be a curved surface such for example as a convexly-curved surface or a concavely-curved surface. The object 2, when viewed in a section taken along a line extending vertically (a Z-axis direction) passing through the center of its planar shape, may be line-symmetrical with respect to an imaginary line extending vertically from the center of the object 2. For example, the object 2 may be a medicine in tablet form. Note that the object 2 is not limited to one whose measurement surface is defined by a curved surface, but may be an object whose measurement surface is defined by a flat surface.

As shown in FIG. 1, the measuring apparatus 1 comprises an optical sensor 3 and a support plate 4. The optical sensor 3 includes a light-emitting element 31 and a light-receiving element 32, and is thus capable of irradiation of the object 2 with light and reception of reflection light reflected from the object 2.

The object 2 is placed on the support plate 4. In other words, the support plate 4 is able to support the object 2. As shown in FIGS. 2 and 4, the optical sensor 3 is located above the support plate 4 for irradiation of the object 2 placed on the support plate 4 with light, for example. Thereby, the measuring apparatus 1 is capable of the measurement of the surface condition of the object 2.

For example, the light-emitting element 31 of the optical sensor 3 may be a light-emitting diode (LED) or a laser diode (LD). For example, the light-receiving element 32 of the optical sensor 3 may be a photodiode (PD) or a phototransistor (PT). The light-emitting element 31 and the light-receiving element 32 may be mounted on their respective wiring substrates as discrete components. Moreover, the light-emitting element 31 and the light-receiving element 32 may be formed on a single wafer.

The optical sensor 3 of this embodiment is constituted by forming the light-emitting element 31 and the light-receiving element 32 on one substrate 33 (wafer) in a single-piece construction. More specifically, the light-emitting element 31 can be formed by placing a stack of a plurality of semiconductor layers on the upper surface of the substrate 33 composed of a semiconductor material of one conductivity type. Moreover, the light-receiving element 32 can be formed by doping impurities of reverse conductivity type into a region of the upper surface of the substrate 33 adjacent to the light-emitting element 31. Thus, by forming the light-emitting element 31 and the light-receiving element 32 that constitute one optical sensor 3 on a single substrate 33, it is possible to dispose the light-emitting element 31 and the light-receiving element 32 in proximity to each other. Thereby, the optical sensor 3 can be miniaturized, wherefore a plurality of optical sensors 3 can be installed in the measuring apparatus 1. Hence, even when performing measurement on a small object such for example as a tablet, the plurality of optical sensors 3 can be used simultaneously for the measurement.

The optical sensor 3, while having at least one light-emitting element 31 and at least one light-receiving element 32, may comprise a plurality of light-emitting elements 31 and a plurality of light-receiving elements 32. As shown in FIG. 5A, the optical sensor 3 of this embodiment has one light-emitting element 31 and two light-receiving elements 32. In the optical sensor 3 of this embodiment, one of the light-receiving elements 32 receives specular reflected light, and the other receives diffuse reflected light, wherefore the measurement accuracy can be improved.

The optical sensor 3 of this embodiment has an electrode pattern 34 disposed on the substrate 33 so as to be electrically connected to the light-emitting element 31 and the light-receiving element 32. The electrode pattern 34 supplies electric current for driving the light-emitting element 31, and takes out electric current resulting from the reception of light by the light-receiving element 32.

For example, the substrate 33 can be composed of a silicon (Si) wafer doped with n-type impurities or p-type impurities. The substrate 33 of this embodiment is formed of an n-type semiconductor material. To be more specific, the substrate 33 is composed of a silicon (Si) wafer doped with n-type impurities. As n-type impurities, for example, it is possible to use phosphorus (P), nitrogen (N), arsenic (As), antimony (Sb), and bismuth (Bi).

As shown in FIG. 5B, the light-emitting element 31 can be formed by laminating a buffer layer 31a, an n-type contact layer 31b, an n-type clad layer 31c, an active layer 31d, a p-type clad layer 31e, and a p-type contact layer 31f one after another on the substrate 33. For example, the light-emitting element 31 can be designed to emit light with wavelengths of 0.7 μm or more to 2.5 μm or less.

The buffer layer 31a is able to reduce the difference in lattice constant between the substrate 33 and the n-type contact layer 31b. The buffer layer 31a can be formed of gallium arsenide (GaAs), for example.

The n-type contact layer 31b is able to permit electrical conduction between the light-emitting element 31 and the electrode pattern 34. For example, the n-type contact layer 31b can be formed of gallium arsenide (GaAs) doped with n-type impurities such as silicon (Si) or selenium (Se).

The n-type clad layer 31c is able to confine holes in the active layer 31d. For example, the n-type clad layer 31c can be formed of aluminum gallium arsenide (AlGaAs) doped with n-type impurities such as silicon (Si) or selenium (Se).

The active layer 31d is able to emit light under concentration and recombination of electrons and holes. The active layer 30d can be formed of aluminum gallium arsenide (AlGaAs), for example.

The p-type clad layer 31e is able to confine electrons in the active layer 31d. For example, the p-type clad layer 31e can be formed of aluminum gallium arsenide (AlGaAs) doped with p-type impurities such as zinc (Zn), magnesium (Mg), or carbon (C).

The p-type contact layer 31f is able to permit electrical conduction between the light-emitting element 31 and the electrode pattern 34. For example, the p-type contact layer 31f can be formed of aluminum gallium arsenide (AlGaAs) doped with p-type impurities such as zinc (Zn), magnesium (Mg), or carbon (C).

The support plate 4 is able to support the object 2. The support plate 4 can be rotated about an axis of rotation extending vertically from a central portion of an upper surface thereof. In other words, the support plate 4 is able to rotate on an axis thereof. The object 2 is mounted on the central portion of the upper surface of the support plate 4. Thereby, as the object 2, now positioned so that, for example, the vertex of the curved surface thereof lies on the axis of rotation of the support plate 4, is rotated in synchronism with the rotation of the support plate 4, it is possible to measure the surface condition of a region of the object 2 along the direction of rotation. That is, in contrast to the case of moving the object 2 rectilinearly, variations in the distance between the optical sensor 3 and the object 2 can be reduced, with a consequent reduction in variations in the angle formed between the optical axis of irradiation light and a normal at a point of measurement. This facilitates the reception of reflected light by the light-receiving element 32, wherefore the measuring apparatus 1 achieves measurement on the object 2.

The light-emitting element 31 may be positioned so that the optical axis of light with which the object 2 is irradiated will not be intersected by the axis of rotation of the support plate 4 at the upper surface of the object 2. This makes it possible to ensure a wider measurement region of the object 2.

The range of irradiation of light from the light-emitting element 31 may cover the axis of rotation at the upper surface of the object 2. Thereby, it is also possible to measure the surface condition of the vertex of the object 2. In the case where the range of irradiation of light from the light-emitting element 31 covers the axis of rotation, the measurement region of the object 2 can be defined by a circular shape. On the other hand, in a case where the axis of rotation falls outside the range of irradiation of light from the light-emitting element 31, the measurement region of the object 2 can be defined by an annular shape. For example, the range of irradiation of light from the light-emitting element 31 can be set to fall in a range of 100 μm or more and 1000 μm or less in terms of spot diameter.

The measuring apparatus 1 may comprise the plurality of optical sensors 3. In this embodiment, the measuring apparatus 1 comprises a first optical sensor 3a and a second optical sensor 3b. As shown in FIG. 3, a first irradiation region R1 irradiated by the light-emitting element 31 of the first optical sensor 3a may be located more inwardly than a second irradiation region R2 irradiated by the light-emitting element 31 of the second optical sensor 3b. In other words, the first irradiation region R1 may be brought nearer to the axis of rotation than the second irradiation region R2. This makes it possible to extend the range of measurement performed by the measuring apparatus 1.

The first irradiation region R1 and the second irradiation region R2 may be spaced apart. This makes it possible to restrain the light from the first optical sensor 3a and the light from the second optical sensor 3b from entering other regions than their respective regions.

The first irradiation region R1 and the second irradiation region R2 may be opposed to each other, with the axis of rotation lying in between. This makes it possible to leave an adequately large distance between the first irradiation region R1 and the second irradiation region R2, and thereby restrain the light from the first optical sensor 3a and the light from the second optical sensor 3b from being received as stray light by other optical sensors 3.

As shown in FIG. 3, a first measurement region Ra assigned to the first optical sensor 3a and a second measurement region Rb assigned to the second optical sensor 3b may be spaced apart. Thereby, as compared with a case where the measurement regions are partly overlaid with each other, measurement can be carried out over a wider range.

Meanwhile, the outer edge of the first measurement region Ra of the first optical sensor 3a may be overlaid with the inner edge of the second measurement region Rb of the second optical sensor 3b. This makes it possible to perform measurement on the surface of the object 2 thoroughly, and thereby achieve in-depth surface condition measurement.

The support plate 4 may be rendered movable in a planar direction (the direction of X-Y plane). Thereby, when placing the object 2 on the support plate 4, it is possible to draw the support plate 4 for convenience of the placement of the object 2, and thereby increase the operation efficiency.

The support plate 4 may be black-colored. This makes it possible to reduce reflection of light incident on the support plate 4, and thereby restrain unnecessary light from entering the light-receiving element 32 of the optical sensor 3. Moreover, from the standpoint of reducing reflection of light incident on the support plate 4, the upper surface of the support plate 4 may be embossed. The support plate 4 can be formed of a metal material such as aluminum.

The support plate 4 may comprise a projection located on the edge of the region of placement of the object 2. This facilitates the positioning of the object 2, with a consequent increase in operation efficiency. Moreover, in the case of forming a projection on the support plate 4, the projection may be given a height which is smaller than the thickness of the object 2. This makes it possible to keep the projection out of the optical path of the optical sensor 3. For example, the height of the projection is set to be less than or equal to ½ times the thickness of the object 2.

The measuring apparatus 1 further comprises a control circuit 5 for controlling the optical sensor 3. The control circuit 5 is electrically connected with the electrode pattern 34 of the optical sensor 3, and includes, for example, a driving circuit for driving the light-emitting element 31, an operation circuit for processing electric current from the light-receiving element 32 or a communication circuit for conducting communications with external equipment, and so forth.

The measuring apparatus 1 further comprises a support member 6 which extends vertically and serves as a support for the measuring apparatus 1, and a securing member 7 which extends in the planar direction from the support member 6 and secures the optical sensor 3. For example, the support member 6 is shaped in a column or a plate. The support member 6 is formed of a metal material such as aluminum. Moreover, from the standpoint of reducing reflection of light incident on the support member 6, the support member 6 may be black-colored, and also, a surface thereof may be embossed.

The support member 6 may be expandable and contractable in the vertical direction. This facilitates the adjustment of the focal length of the optical sensor 3 relative to the object 2. While, in this embodiment, the focal length of the optical sensor 3 is adjustable with expansion and contraction of the support member 6, in the alternative, the focal length of the optical sensor 3 may be adjusted by setting the support plate 4 so as to movable in the vertical direction.

One end of the securing member 7 is fixed to the support member 6, and, the other end of the securing member 7 is located in a region above the support plate 4. The optical sensor 3 can be attached to the other end of the securing member 7 via an adhesive formed of a resin material. The optical sensor 3 is attached to the securing member 7 so as to be opposed to the support plate 4, with the securing member 7 lying in between. The other end of the securing member 7 has an opening, whereby the optical sensor 3 is able to irradiate the object 2 with light and receive reflected light through the opening of the securing member 7.

The securing member 7 can be shaped in a rod or a plate. For example, the securing member 7 can be formed of a metal material such as aluminum. Moreover, from the standpoint of reducing reflection of light incident on the securing member 7, the securing member 7 may be black-colored, and also a surface thereof may be embossed.

The securing member 7 may be rotatable about an axis extending along a longitudinal axis. This facilitates the adjustment of the angle formed between the optical axis of irradiation light to the object 2 and a normal at a point of measurement, or equivalently, facilitates the adjustment of a location of irradiation of the object 2 with the light emitted from the light-emitting element 31.

The securing member 7 may be movable in a planar direction along the upper surface of the support plate 4. This facilitates the adjustment of a location of irradiation of the object 2 with the light emitted from the light-emitting element 31.

The securing member 7 may be plate-shaped. This makes it possible to define the upper surface of the securing member 7 as a reference surface for the installation of the optical sensor 3, and thereby increase the efficiency of operation.

In the case where the securing member 7 is plate-shaped, the optical sensor 3 may be disposed so that the principal surface of the substrate 33 stays along the principal surface of the securing member 7. Since the optical sensor 3 of this embodiment is composed of the light-emitting element 31 and the light-receiving element 32 formed on one substrate 33 in a single-piece construction, it follows that the optical path of the optical sensor 3 depends upon the orientation of the principal surface of the substrate 33. Hence, with this arrangement, the orientation of the optical sensor 3 can by adjusted by making adjustment to the orientation of the principal surface (lower surface) of the securing member 7, with a consequent increase in operation efficiency.

The measuring apparatus 1 further comprises a mount 8 for supporting the support plate 4. For example, the mount 8 is plate-shaped. For example, the mount 8 is formed of a metal material such as aluminum. Moreover, from the standpoint of reducing reflection of light incident on the mount 8, the mount 8 may be black-colored, and also its surface may be embossed.

<Measuring Method>

The following describes a method for the measurement of the surface of the object 2 using the measuring apparatus 1 according to the present disclosure. It should be understood that the invention is not limited to this embodiment, and that various changes, modifications, and improvements are possible without departing from the scope of the invention.

(1) There are prepared the measuring apparatus 1 and the object 2 in which the surface condition is measured using the measuring apparatus 1. Then, the object 2 is placed on the support plate 4 of the measuring apparatus 1. In cases where a measurement surface of the object 2 is a convexly-curved surface or a concavely-curved surface, the object 2 may be positioned so that the vertex of the curved surface thereof coincides with the axis of rotation of the support plate 4. As the object 2, a medicine in tablet form can be given by way of example.

(2) The light-emitting element 31 of the optical sensor 3 of the measuring apparatus 1 is secured in place. The light-emitting element 31 is secured in a position where one point of the object 2 is irradiated with light. That area of the object 2 irradiated with light from the light-emitting element 31 is where it is desired that the measurement of the surface condition of the object 2 is performed. In cases where the measuring apparatus 1 has a plurality of optical sensors 3, the individual optical sensors 3 are secured so that different areas of the object 2 are irradiated with light.

(3) While the support plate 4 is rotated in a state where the optical sensor 3 is secured in place, reflected light from the object 2 is received by the light-receiving element 32 of the optical sensor 3. Upon rotating the support plate 4, the object 2 can be rotated simultaneously. Thereby, it is possible to measure the surface condition of the surface of the object 2 along the direction of rotation by performing arithmetic operation on output of current produced by the light-receiving element 32 in accordance with the quantity of light received by the light-receiving element 32 via the control circuit 5.

REFERENCE SIGNS LIST

1: Measuring apparatus
2: Object
3: Optical sensor
31: Light-emitting element
32: Light-receiving element
33: Substrate
34: Electrode pattern
3a: First optical sensor
3b: Second optical sensor
4: Support plate
5: Control circuit
6: Support member
7: Securing member
8: Mount
R1: First irradiation region
R2: Second irradiation region
Ra: First measurement region
Rb: Second measurement region

The invention claimed is:

1. A measuring apparatus, comprising:
a support plate comprising an upper surface on a central portion of which an object is to be mounted, the support plate being rotatable about an axis of rotation extending vertically from the central portion; and
an optical sensor secured to an end of a securing member which extends in a planar direction, the optical sensor disposed above and opposed to the support plate, the optical sensor comprising a light-emitting element configured to irradiate the object with light, a first light-receiving element configured to receive specular reflected light reflected from the object, and a second light-receiving element configured to receive diffuse reflected light reflected from the object,
wherein the light-emitting element, the first light-receiving element, and the second light-receiving element are formed on a single substrate, and
wherein the first light-receiving element is positioned on an opposite side of the light-emitting element than the second light-receiving element.

2. The measuring apparatus according to claim 1, wherein the light-emitting element is positioned so that an optical axis of light, with which the object is irradiated, does not intersect the axis of rotation at an upper surface of the object.

3. The measuring apparatus according to claim 1, comprising a first optical sensor and a second optical sensor, wherein each of the first optical sensor and the second optical sensor comprises a respective light-emitting element, first light-receiving element, and second light-receiving element formed on a respective single substrate, and wherein a first irradiation region irradiated by the light-emitting element of the first optical sensor is located more inwardly than a second irradiation region irradiated by the light-emitting element of the second optical sensor.

4. The measuring apparatus according to claim 3, wherein the first irradiation region and the second irradiation region are spaced apart by a non-zero distance.

5. The measuring apparatus according to claim 4, wherein the first irradiation region is positioned on an opposite side of the axis of rotation than the second irradiation region.

6. The measuring apparatus according to claim 1, wherein the object is a tablet.

7. A measuring method, comprising:
placing an object on the support plate of the measuring apparatus according to claim 1;
securing the optical sensor of the measuring apparatus in a position where one point of the object is irradiated with light from the light-emitting element; and
receiving reflection light from the object by both the first light-receiving element and the second light-receiving element of the optical sensor while rotating the support plate in a state where the optical sensor is secured in the position.

8. The measuring apparatus according to claim 1, wherein the optical sensor is attached to the securing member on an opposite side of the securing member from the support plate, such that the securing member is positioned between the optical sensor and the support plate, and wherein the securing member comprises an opening between the optical sensor and the support plate, such that the light-emitting element is able to irradiate the object with light through the opening and the first and second light-receiving elements are able to receive light reflected from the object through the opening.

* * * * *